US006852109B2

(12) United States Patent
Winston et al.

(10) Patent No.: US 6,852,109 B2
(45) Date of Patent: Feb. 8, 2005

(54) RADIO FREQUENCY GUIDE WIRE ASSEMBLY WITH OPTICAL COHERENCE REFLECTOMETRY GUIDANCE

(75) Inventors: Thomas R. Winston, Leawood, KS (US); John M. Neet, Lawrence, KS (US)

(73) Assignee: Intraluminal Therapeutics, Inc., Kansas City, KS (US)

( * ) Notice: Subject to any disclaimer, the term of this patent is extended or adjusted under 35 U.S.C. 154(b) by 160 days.

(21) Appl. No.: 10/166,900

(22) Filed: Jun. 11, 2002

(65) Prior Publication Data

US 2003/0229342 A1 Dec. 11, 2003

(51) Int. Cl.[7] ............................................. A61B 18/18
(52) U.S. Cl. ....................................................... 606/41
(58) Field of Search ..................... 606/27–52

(56) References Cited

U.S. PATENT DOCUMENTS

| | | | |
|---|---|---|---|
| 3,595,239 A | | 7/1971 | Petersen |
| 4,532,924 A | | 8/1985 | Auth |
| 4,682,596 A | | 7/1987 | Bales et al. |
| 5,098,431 A | | 3/1992 | Rydell |
| 5,321,501 A | * | 6/1994 | Swanson et al. ............ 356/479 |
| 5,439,000 A | * | 8/1995 | Gunderson et al. ......... 600/473 |
| 5,454,809 A | | 10/1995 | Janssen |
| 5,514,128 A | * | 5/1996 | Hillsman et al. ............... 606/7 |
| 5,601,087 A | * | 2/1997 | Gunderson et al. ......... 600/473 |
| 5,722,403 A | * | 3/1998 | McGee et al. ............... 600/373 |
| 5,743,900 A | | 4/1998 | Hara |
| 5,749,914 A | | 5/1998 | Janssen |
| 5,762,609 A | * | 6/1998 | Benaron et al. ............. 600/473 |
| 5,782,826 A | * | 7/1998 | Swanson ....................... 606/34 |
| 6,117,128 A | * | 9/2000 | Gregory ......................... 606/7 |
| 6,175,669 B1 | * | 1/2001 | Colston et al. ............... 385/12 |
| 6,193,676 B1 | | 2/2001 | Winston et al. |
| 6,228,081 B1 | * | 5/2001 | Goble .......................... 606/34 |
| 6,458,088 B1 | * | 10/2002 | Hurtak et al. ............... 600/585 |
| 6,485,488 B1 | * | 11/2002 | Muller et al. ................. 606/41 |
| 6,660,001 B2 | | 12/2003 | Gregory |

* cited by examiner

Primary Examiner—Beverly M. Flanagan
Assistant Examiner—Pete Vrettakos
(74) Attorney, Agent, or Firm—Armstrong Teasdale LLP

(57) ABSTRACT

A guide wire assembly includes a guide wire, an optical fiber, and an insulating coating. The guide wire has a distal end, a proximal end, and a bore extending through the wire between the distal and proximal ends. The an optical fiber also includes a distal end and a proximal end and is located within the bore of the guide wire. The optical fiber extends at least between the distal and proximal ends of the guide wire. The insulating coating is around an outside diameter of the guide wire, and is applied such that the distal ends of the guide wire and optical fiber are exposed.

20 Claims, 3 Drawing Sheets

RADIO FREQUENCY GUIDE WIRE ASSEMBLY WITH OPTICAL COHERENCE REFLECTOMETRY GUIDANCE

BACKGROUND OF THE INVENTION

This invention relates generally to medical guide wires and catheters and more particularly, to guiding assemblies and guiding methods for guide wires.

Disease processes, e.g., tumors, inflammation of lymph nodes, and plaque build-up in arteries, often afflict the human body. As one specific example, atherosclerotic plaque is known to build up in the walls of arteries in the human body. Such plaque build-up restricts circulation and often causes cardiovascular problems, especially when the build-up occurs in coronary arteries.

To treat such disease, it often is necessary to guide a medical device to the diseased site, and then use the medical device to treat the diseased area. Commonly a guide wire is used to help guide other treatment devices. A guide wire typically is required to properly position a catheter in an artery. The guide wire is advanced and forms a path, through the artery and region of plaque build-up. The catheter or other device such as a balloon or rotational atherectomy device is then guided through the artery using the guide wire as a rail.

Known guide wires exist for the treatment of tissue. For example, known guide wires use laser energy to remove plaque build-up on artery walls as the guide wire is advanced. One known catheter includes a laser source and a guide wire body. The guide wire body has a first end, a second end, or head, and several optic fibers extending between the first end and the second end. The laser source is coupled to each of the optic fibers adjacent the catheter body first end and is configured to transmit laser energy simultaneously through the optic fibers.

To remove arterial plaque, for example, the guide wire body is positioned in the artery so that the second end of the guide wire body is adjacent a region of plaque build-up. The laser source is then energized so that laser energy travels through each of the optic fibers and substantially photoablates the plaque adjacent the second end of the catheter body. The guide wire body is then advanced through the region to photoablate the plaque in the entire region.

However, it often is difficult to guide known guide wires through the body without risking damage. For example, known guide wires typically cannot be easily advanced through partially or totally occluded arteries without substantial risk of damaging or puncturing the artery wall. As the guide wire is advanced through the artery, it will encounter obstructions to advancement including plaque build-up or the artery wall itself. However, known guide wires typically do not distinguish between plaque build-up and the artery wall. An operator may therefore incorrectly identify an obstruction as plaque build-up and attempt to push the guide wire through the obstruction, resulting in injury or puncture of the artery wall.

Even if the direction of the artery is known, often it is not possible to pass a guide wire through the occlusion because the lesion is too resistant or it is a refractory lesion. In this case, it would be desirable to have a means to ablate the diseased tissue, but not damage the healthy tissue. Laser energy is known as a means of photoablation of the tissue, healthy or diseased. Likewise, radio frequency energy is known as a means of thermal ablation of the tissue, healthy or diseased.

BRIEF DESCRIPTION OF THE INVENTION

In one embodiment, a guide wire assembly is provided which comprises a guide wire further comprising a distal end, a proximal end, and a bore extending therethrough between the distal end and the proximal end. The guide wire assembly also comprises an optical fiber having a distal end and a proximal end and located within the bore of the guide wire. The optical fiber extends from the distal end of the guide wire to the proximal end of the guide wire. An insulating coating extends around an outside diameter of the guide wire and is applied such that the distal end of the guide wire and the distal end of the optical fiber are exposed.

In another embodiment, a bi-polar guide wire assembly is provided which comprises an inner guide wire further comprising a distal end, a proximal end, and a bore extending therethrough between the distal end and the proximal end. The assembly further comprises an optical fiber comprising a distal end and a proximal end and located within the bore of the inner guide wire. The optical fiber extends at least from the distal end of the inner guide wire to the proximal end of the inner guide wire. The assembly further comprises an insulating layer surrounding the inner guide wire. The insulating layer comprises a distal end and a proximal end. The guide wire assembly also comprises an outer guide wire having a distal end, a proximal end, and a bore extending therethrough between the distal end and the proximal end. The inner guide wire, optical fiber, and insulating layer are positioned within the bore of the outer guide wire.

In still another embodiment, an RF ablation apparatus is provided which comprises a guide wire assembly, an optical coherence reflectometer connected to the proximal end of the optical fiber, and an RF power source connected between the guide wire and a RF power return path.

In a further embodiment, a method for controlling an ablation process, using a radio frequency (RF) ablation system is provided. The system includes a radio frequency power section, an optical coherence reflectometer, a guide wire assembly optically connected to the reflectometer and electrically connected to the RF power source, the electrical connection being controlled through a control switch. The method comprises extending a distal end of the guide wire assembly through diseased artery segments to lesions by percutaneous introduction through a body extremity, using OCR guidance to position the distal end against a lesion, applying RF power at the distal end of the guide wire assembly to ablate the lesion, and removing RF power upon an OCR detection of healthy tissue near the distal end of the guide wire assembly.

In another embodiment, a method for performing a transmyocardial revascularization procedure using a radio frequency (RF) ablation system is provided. The system includes a radio frequency power section, an optical coherence reflectometer (OCR), a guide wire assembly optically connected to the reflectometer and electrically connected to the RF power source, the electrical connection being controlled through a control switch. The method comprises extending a distal end of the guide wire assembly to an inner wall surface of a left ventricle of a heart, applying RF power to the distal end, ablating a hole within the inner wall surface, and using a signal from the OCR to stop ablation at a selected distance from an interface between the myocardium and epicardium.

DETAILED DESCRIPTION OF THE INVENTION

Figure 1:
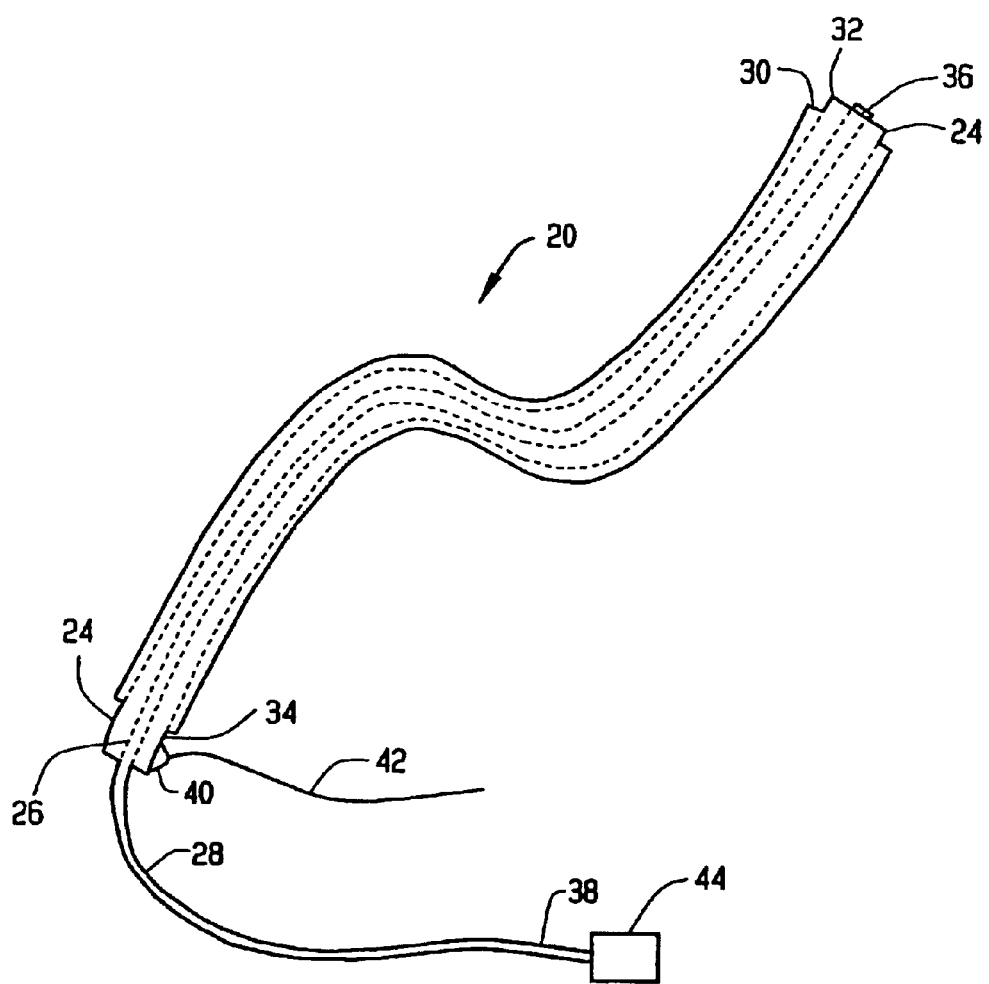
FIG. 1 illustrates a guide wire assembly.

FIG. 1 illustrates one embodiment of a guide wire assembly 20. In one application, guide wire assembly 20 utilizes optical coherence reflectometry (OCR) to control an RF ablation feature implemented using guide wire assembly 20. Referring specifically to guide wire assembly 20, there is included a metal guide wire 24 having a cylindrical bore 26 therethrough. An optical fiber 28 is located within bore 26 of guide wire 24. Guide wire assembly 20 is configured to be inserted into a body passage (not shown) such as a blood vessel. Guide wire assembly 20 further includes an insulation coating 30 extending over guide wire 24 as further described below. Guide wire 24 has a distal end 32 and a proximal end 34 and optical fiber 28 also includes a distal end 36 and a proximal end 38. As referred to herein, "distal end" refers to an end first inserted into the body passage and "proximal" refers to an end opposite the "distal end". Distal ends 32 and 36 are positioned within a blood vessel (not shown) adjacent tissue through which a guide wire is to be advanced, e.g., plaque (not shown). Guide wire 24 may be formed, for example, with a coiled wire, as well known in the art.

Proximal end 34 of guide wire 24 is, in one embodiment, configured with an electrical connector 40, to allow electrical connection of guide wire 24 to an electrical lead 42. Lead 42 is attached to guide wire 24 by at least one of soldering, crimping, and welding to proximal end 34. Lead 42 is terminated with any standard electrical connector for interfacing with RF generation equipment (shown in FIG. 4) used to ablate tissue at distal end 32 of guide wire 24. Similarly, proximal end 38 of optical fiber 28 is configured to be connected to optical equipment 44, for example an optical coherence reflectometer (OCR) (shown in FIG. 4). Integration of optical fiber 28 into guide wire assembly 20, along with OCR, provides a control mechanism for the ablation process by providing reflections of the area in front of guide wire 24. Reflections are used to determine if it is safe to ablate objects, for example, tissue and plaque, within a region. In addition, reflections are used to determine if it is unsafe to ablate objects, for example, healthy tissue (i.e. guide wire 24 is adjacent healthy tissue). In one embodiment, distal end 38 is connected directly to optical equipment 44. In alternative embodiments, distal end 38 is connected to optical equipment 44 through a series of optical interconnections, as is well known in the art.

Figure 2:
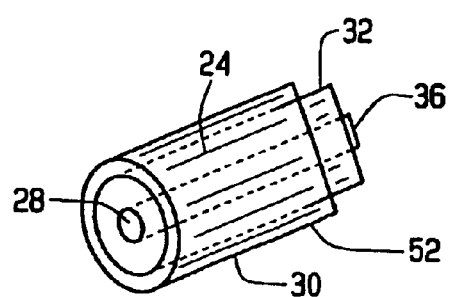
FIG. 2 is a sectional view of the guide wire assembly of FIG. 1.

FIG. 2 is a sectional view of distal end 52 of guide wire assembly 20. Distal end 32 of guide wire 24 and distal end 36 of optical fiber 28 are exposed since insulating coating 30 has been removed at distal end 52 of guide wire assembly 20. In one embodiment, about 0.25 to about 0.001 inch of distal end 32 of metal guide wire 24 is exposed. In another embodiment, about 0.1 to about 0.01 inch of distal end 32 of metal guide wire 24 is exposed. In yet another embodiment, about 0.01 inch of distal end 32 of metal guide wire 24 is exposed. In still another embodiment, about 0.1 inch of distal end 32 of metal guide wire 24 is exposed. In an embodiment not shown insulating coating 30 is configured, either through application or removal after application, such that only a cross section of distal end 32 of metal guide wire 24 and distal end 36 of optical fiber 28 are exposed. In alternative embodiments, insulating coating 30 is one or more of polytetrafluoroethylene (PTFE) material, polyimide, or a conformal coating such as polyparaxylylene (Parylene).

Figure 4:
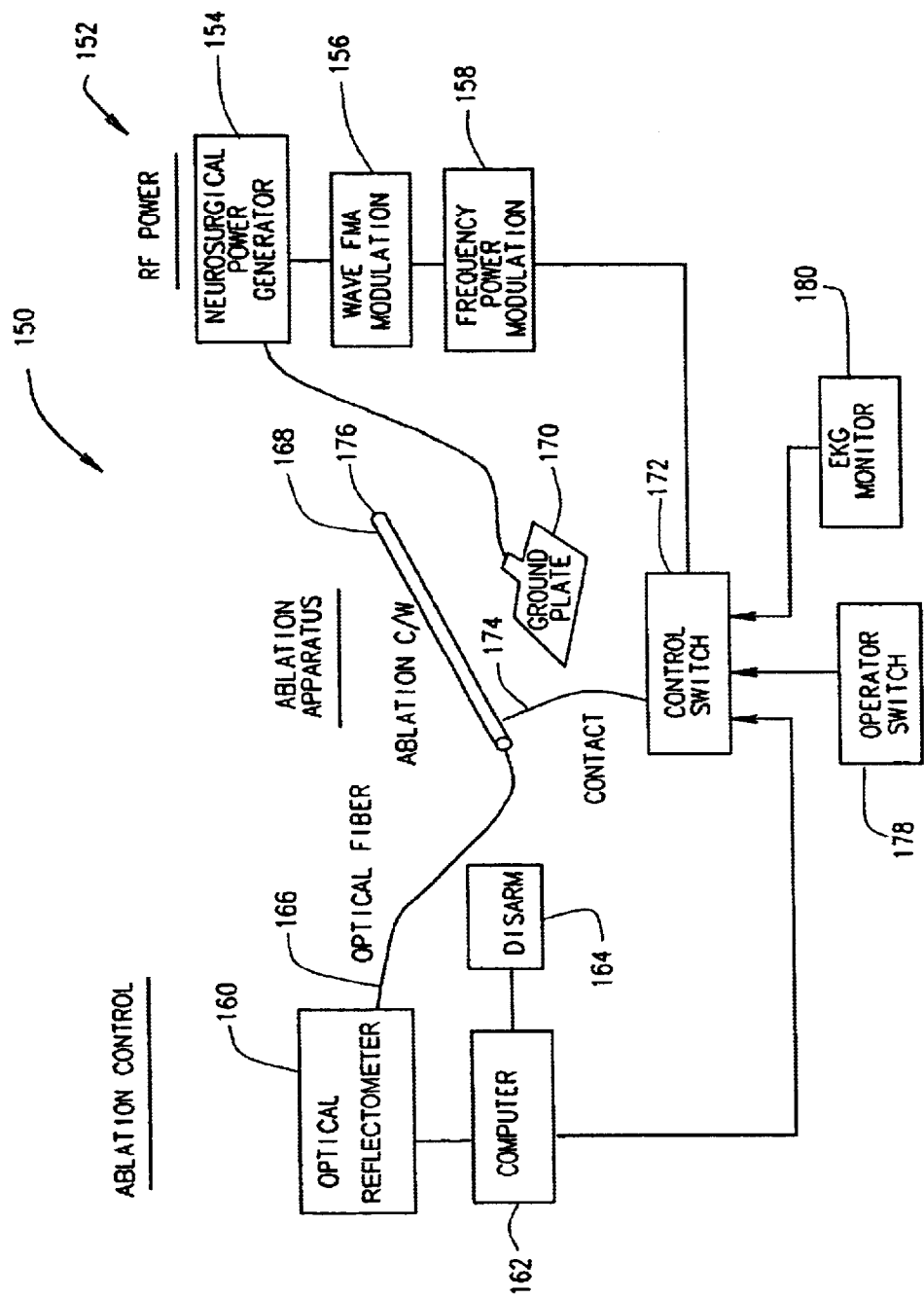
FIG. 4 is a schematic illustration of a radio frequency ablation system.

In one embodiment, guide wire assembly 20 is a monopolar RF guide wire assembly and is used in conjunction with a grounding plate (shown in FIG. 4). The grounding plate contacts a patient and provides a return path for RF power transmitted at distal end 32 of metal guide wire 24 during an ablation process.

Figure 3:
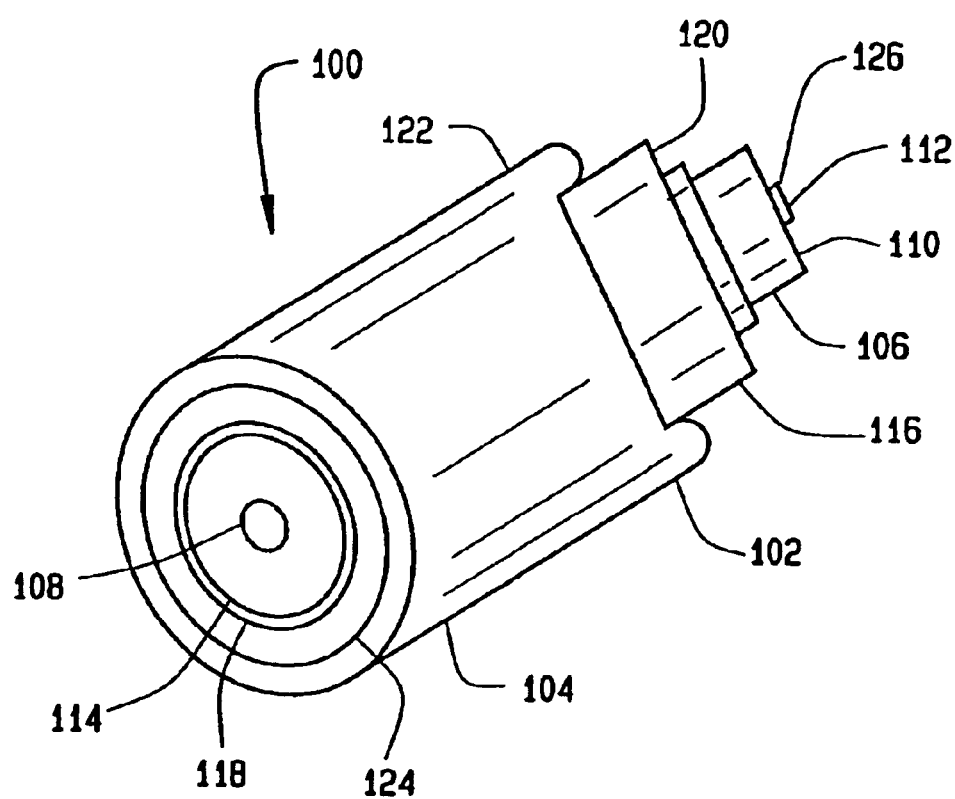
FIG. 3 is a sectional view of a bipolar guide wire assembly.

FIG. 3 is a sectional view of a distal end 102 of a bi-polar guide wire assembly 104. Assembly 104 includes an inner guide wire 106 having a bore 108 therethrough from a distal end 110 to a proximal end (not shown). An optical fiber 112 is within bore 108 of inner guide wire 106 and extends at least from distal end 110 to the proximal end (not shown) of assembly 104. Inner guide wire 106 is insulated about its circumference and along its length with an insulating layer 114. In alternative embodiments, insulating coating 114 is one or more of polytetrafluoroethylene (PTFE) material, polyimide, epoxy, nylon, rubber or a conformal coating such as polyparaxylylene (Parylene). Insulating layer 114 of a length which prevents electrical contact from occurring between inner guide wire 106 and an outer guide wire 116. Outer guide wire 116 includes a bore 118 therethrough from a distal end 120 to a proximal end (not shown). In the embodiment shown, optical fiber 112, inner guide wire 106, and insulating layer 114 are located within bore 118 of outer guide wire 116. Guide wire assembly 104 further includes an insulating coating 122, similar in composition and application to insulating coating 30 (shown in FIG. 2), which insulates at least a portion of an outside diameter 124 of outer guide wire 116.

Distal end 110 of inner guide wire 106, distal end 120 of outer guide wire 116, and distal end 126 of optical fiber 112 are exposed as insulating coating 122 has been removed at distal end 102 of guide wire assembly 104. To expose distal end 110 of inner guide wire 106 a portion of insulating layer 114 is also removed. In one embodiment, from about 0.001 inch to about 0.25 inch of distal ends, 110 and 120 of guide wires 106 and 116, respectively, are exposed. In another embodiment, from about 0.01 inch to about 0.1 inch of distal ends 110 and 120 of guide wires 106 and 116, respectively, are exposed. In still another embodiment, not shown, insulating coating 122 is applied such that only a cross section of distal ends 110, 120 of guide wires 106, 116, an end of insulating layer 114, and distal end 126 of optical fiber 112 are exposed. In alternative embodiments, insulating coating 122 is one or more of polytetrafluoroethylene (PTFE) material, polyimide, or a conformal coating such as polyparaxylylene (Parylene).

Guide wire assembly 104 is a bi-polar RF guide wire assembly. In one embodiment, inner guide wire 106 provides a return path for RF power transmitted at distal end 120 of outer guide wire 116 during an ablation process. In an alternative embodiment, polarity of guide wire assembly 104 may be reversed, with outer guide wire 116 providing a return path for RF power and inner guide wire 106 transmitting the RF power. In such an embodiment, insulating coating 122 is optional. In specific embodiments, bi-polar guide wire assembly 104 has a diameter of at least 0.010 inches.

Optical fibers 36 (shown in FIGS. 1 and 2) and 112 are configured to emit energy waves substantially co-axially with respect to the distal ends of guide wire assemblies 20 (shown in FIG. 1) and 104. In one embodiment, an illumination source is a low coherent illumination source, for example, a light emitting diode as known in the art. Optical fibers 28 (shown in FIG. 1) and 112 are fabricated from drawn or extruded glass or plastic having a central core and a cladding of a lower refractive index material to promote internal reflection. In one embodiment, optical fibers 28 and 112 are polarization-preserving single mode optic fibers which preserve the plane of polarization of a light beam as it propagates along the length of a fiber. Polarization-preserving optic fibers maintain the polarization of the light beam by having asymmetry in the fiber structure, either in the overall shape of the fiber, or in the configuration of the cladding with respect to the central core. In one embodiment, the diameter of each of fibers 28 and 112 is about 125 microns, but the diameter may vary.

FIG. 4 is a radio frequency (RF) ablation system 150 which incorporates optical coherence reflectometry. System 150 includes an RF power section 152, which includes an electrosurgical power generator 154, a waveform modulator 156 and a frequency power modulator 158. System 150 further includes an optical coherence reflectometer 160 whose operation is controlled through computer 162 which has a display 164. Reflectometer 160 is optically connected to optical fiber 166, which extends to proximal ends of fibers 28 and 112 (shown in FIGS. 2 and 3 respectively), which form a portion of guide wire 168. Guide wire 168, is in alternative embodiments, one of guide wire assemblies 20 and 104 (described in FIGS. 1 and 3). A ground plate 170 provides a return path for RF power when an embodiment of system 150 incorporates guide wire assembly 20.

Electrosurgical power generator 154 provides RF power and typically operates with a frequency range of about 200 kHz to about 35 MHz. In the ablation process, a more typical frequency range is about 500 kHz to about 2 MHz. Open circuit voltages range from about 100 V to about 10 kV. Output of generator 154 is waveform modulated so that desired ablation effects are obtained. Coagulation is achieved by using dampened sinusoidal pulses to modulate the RF power at lower frequencies. In one embodiment, the RF output is in a range of about 200 kHz to about 2 MHz and pulsed (modulated) by wave form modulator 156 at a rate of about 100 Hz to about 10 kHz. Cutting (ablation) is achieved through higher RF power output at higher frequencies. In one embodiment, frequencies used for ablation range from about 500 kHz to about 2.5 MHz and an open circuit voltage as high as 1 kV. Although sinusoidal waves are one embodiment of waveform modulation, other waveform modulation patterns are used in alternative embodiments.

In one embodiment, optical fiber 166 connects Optical Coherence Reflectometer (OCR) 160 to guide wire 168 to allow visualization of the tissue in front of guide wire 168. Low coherence near infrared light from a light emitting diode (not shown) is input into the optical fiber system. In OCR 160, the low coherence light is divided into two beams with one beam being diverted to optical fiber 166 and thus to guide wire 168. The second (reference) beam stays within OCR 160 in a fiber that has a path length equivalent to a path length of the fiber from the OCR 160, through fiber 166 and guide wire 168. In one embodiment, OCR 160 is configured in a Michelson interferometer configuration. The optical path length in the second (reference) beam is varied, either mechanically by moving a mirror at the end of the fiber within OCR 160 or by stretching the fiber, for example, as is done with PZT stretchers. The effect is that the light scattered by the tissue back into guide wire 168 recombines with the light from the second beam such that an interference pattern is generated for light that is scattered from the tissue at an equivalent path length as the second beam. By knowingly varying the path length of the second (reference) beam, an interference intensity versus distance profile can be generated.

It has been shown that a light scattering intensity increases from the normal arterial wall compared to the scattering properties of the occlusive materials. This same characteristic can be shown for other interfaces such as the boundary of tumor and healthy tissue. An algorithm configures computer 162 to analyze the scattering intensity versus distance data to determine if there is a sharp increase in the relative scattering within the interferometer sweep. If a sharp increase is detected, the operator is warned that the arterial wall is close and a control signal which enables RF energy output from generator 154 changes state, stopping RF output from generator 154 and therefore stopping delivery of RF energy to guide wire 168.

In an alternative embodiment, output of generator 154 is frequency power modulated to deliver bursts of RF power followed by deadtime, thereby allowing any heat present near the ablation area to dissipate. Utilization of deadtime prevents heat buildup that could damage adjacent tissue.

In different embodiments, RF power output of generator 154 is gated by different logical controls. A control switch 172 provides the gating for the different controls. A first gating mechanism is an OCR signal received over optical fiber 166 at OCR 160. The OCR signal is a feedback signal which is monitored through utilization of computer 162. Computer 162 also provides a gating signal to control switch 172, controlling RF output over an electrical contact 174 to assure that a distal tip 176 of guide wire 168 contacts tissue to be ablated. The OCR signal is further monitored to assure that an interface between unhealthy and healthy tissue is not near distal tip 176 thus assuring that the ablation will only affect unhealthy (targeted) tissue. In the case of a total occlusion, the OCR signal is monitored to assure that the normal artery wall (media) is not near, whereas in a percutaneous transmyocardial revascularization (PTMR) procedure the OCR signal is monitored for an epicardium interface while myocardial tissue is being ablated. The OCR signal, which is monitored utilizing an algorithm running in computer 162, yields a go/no-go signal for gating the RF power.

In a second embodiment, RF power output transferred to distal tip 176 through electrical contact 174 is controlled using an operator switch 178. In one embodiment, operator switch 178 is a foot switch or any switch accessible by an operator. In another embodiment, control of the RF power applied for ablation by an operator is contemplated. In such an embodiment, switch 178 is integrated into a catheter handle (not shown) which is utilized for advancement of guide wire 168. In such an embodiment, when the operator advances guide wire 168, switch 178 closes allowing the RF power to ablate with the advancement.

In still another embodiment, control switch 172 is gated by incorporation of an EKG monitor 180 to assure that RF power is not applied during the S-T segment period. The heart is most sensitive to electrical stimulation during this time and by blocking RF output during this period, a patient is protected from arrhythmias.

It is to be appreciated that any combination of the above described gating mechanisms can be used, and which gating mechanisms are used in any one application depends on the particular application and risk to the patient. In the above described embodiments, computer 162 is configured to generate data from the ablation process and display the data on display 164, thereby providing an operator feedback regarding an ablation process.

RF ablation system 150 with incorporation of OCR guidance has many applications in medical practice. System 150 can be used wherever a conventional guide wire is used, but offers the additional features of tissue ablation and guidance. It will be appreciated that the examples described below are not limiting, but rather, the examples are for purposes of illustration. For example, atherosclerotic disease severely impairs the arterial functions with the formation of plaques, atheromas, and thrombus in the vessel. This disease is routinely treated by interventional angioplasty. In such a treatment, traditional guide wires are threaded through the diseased artery segments by percutaneous introduction through a body extremity. Angioplasty balloons or other atherectomy devices are used to dilate and re-establish flow within the artery.

However, when treated using the OCR guided RF ablation of system 150, guide wire 168 is used to cross highly resistant lesions. OCR guidance assures the operator that guide wire 168 is within the lumen and RF ablation provides a hole within the lesions for the wire to pass through. The operator identifies diseased artery segments under angiographic examination with x-ray imaging and the introduction of contrast into the blood field. Commercially available introducers and guide catheters are then used to establish access to the diseased region. The OCR/RF guide wire 168 of system 150 is guided to the targeted segment under x-ray imaging and placed adjacent the diseased blockage. The operator then attempts to push guide wire 168 into the lesion using the OCR signal to assure that the wire is within the lumen and not too close to the normal artery wall. If the lesion is too resistant, wire 168 will buckle or the supporting catheter will be forced back (proximal), rather than guide wire 168 advancing. In such a case, the operator selects the RF ablation mode. The OCR processing in computer 162 assures that distal tip 176 of guide wire 168 is against tissue and that the artery wall is not too close. If necessary, the patient's EKG is monitored with monitor 180 to trigger the RF power during a non-critical time of the coronary cycle. Distal tip 176, when energized, will create a small spark ablating the tissue in front of the wire. The energy is pulsed, as described above, to allow generated heat to dissipate, preventing collateral tissue damage from excessive heat storage. The process is repeated to create a hole through the lesion through which wire 168 can pass. If the OCR signal detects a normal artery wall, RF power is removed to prevent damage to the artery.

Transmyocardial revascularization (TMR) is a recent therapy for patients that have severe angina and other treatment modalities have failed. Small channels are ablated into the myocardium to revascularize the ischemic tissue. The OCR/RF guide wire system 150 is used to create the channels or holes within the myorcardial tissue. Catheters are used to gain percutaneous access to the left ventricle of the heart. Guide wire 168 is introduced through the catheter and positioned adjacent to the inner wall surface. Wire 168 is positioned by x-ray imaging, and advanced into the tissue while energized, ablating a hole. The OCR signal is used to control the depth of the hole. Ablation is stopped when the interface between the myocardium and epicardium is approached, preventing perforation of the heart. The OCR signal is also used to prevent perforation of a coronary artery.

OCR/RF guide wire system 150 provides a safe method for advancement of guide wire 168 into a vessel. Guide wire 168 further is a mechanism which provides information to help an operator distinguish among the types of obstructions which might be obstructing advancement of the guide wire. However, it is to be understood that the above described guide wire and methods for implementing treatments which implement system 150 are exemplary and other embodiments are possible. For example, in another embodiment, guide wire 168 may be made with a harder and less flexible distal end (for example, made of hardened steel) to make it more suitable to go through a partially occluded artery. The guide wire may also be coated with a friction reducing material such as, for example, a polymer or a hydrophilic coating as known in the art. The coating reduces the surface friction to ease advancing the guide wire further into the vessel. The guide wire may also include a thin metal wire positioned next to the fiber optic which can be pulled back making the guide wire end very floppy. The metal wire, when extended, stiffens the distal end portion of the guide wire.

While the invention has been described in terms of various specific embodiments, those skilled in the art will recognize that the invention can be practiced with modification within the spirit and scope of the claims.

What is claimed is:

1. A radio frequency (RF) ablation apparatus comprising:
   a guide wire assembly comprising:
      a guide wire comprising a distal end, a proximal end, and a bore extending therethrough between said distal end and said proximal end;
      an optical fiber comprising a distal end and a proximal end and located within said bore of said guide wire, said optical fiber extending at least to said distal end of said guide wire; and
      an insulating coating surrounding an outside diameter of said guide wire, said insulating coating configured such that said distal end of said guide wire and said distal end of said optical fiber are exposed;
   an optical coherence reflectometer optically connected to a proximal end of said guide wire assembly; and
   an RF power source electrically connected between said guide wire assembly and a return path for RF power.

2. An RF ablation apparatus according to claim 1 wherein said RF power source comprises:
   an electrosurgical RF power generator;
   a wave form modulator; and
   a frequency power modulator.

3. An RF ablation apparatus according to claim 2 wherein said electrosurgical power generator has a frequency range of about 200 kHz to about 35 MHz.

4. An RF ablation apparatus according to claim 2 wherein said wave form modulator is configured to modulate said electrosurgical RF power generator from about 100 Hz to about 10 kHz.

5. An RF ablation apparatus according to claim 1 wherein the RF return path comprises a grounding plate.

6. An RF ablation apparatus according to claim 1 wherein said guide wire is an inner guide wire and said guide wire assembly further comprises:
   an outer guide wire comprising a distal end, a proximal end, and a bore extending therethrough between said distal end and said proximal end, said inner guide wire, said optical fiber, and said insulating layer positioned within said bore of said outer guide wire.

7. An RF ablation apparatus according to claim 6 wherein said guide wire assembly comprises an insulating coating around an outside diameter of said outer guide wire, said insulating coating configured such that at least said distal end of said inner guide wire, said distal end of said outer guide wire, said distal end of said insulating layer, and said distal end of said optical fiber are exposed, one of said inner guide wire and said outer guide wire providing the return path for RF power.

8. An RF ablation apparatus according to claim 1 further comprising an EKG monitor, said monitor configured to gate RF power from said RF power source to ensure RF power is not applied during an S-T segment period.

9. An RF ablation apparatus according to claim 1 further comprising an operator switch, said switch configured to gate RF power from said RF power source upon closure of the switch by an operator.

10. An RF ablation apparatus according to claim 1 further comprising a computer coupled to said optical coherence reflectometer (OCR), said computer configured to gate RF power from said RF power source based upon an OCR feedback signal.

11. An RF ablation apparatus according to claim 10 wherein said computer is configured with an algorithm to analyze a scattering intensity against distance data received from said OCR to determine any increases in relative scattering.

12. An RF ablation apparatus according to claim 11 wherein if an increase in relative scattering is detected, said computer is configured to warn an operator that an arterial wall is close to said distal end of said guide wire cause RF power to be removed from said guide wire assembly.

13. An RF ablation apparatus according to claim 10 wherein the OCR feedback signal is monitored to ensure that a distal tip of said guide wire assembly is in contact with tissue to be ablated.

14. An RF ablation apparatus according to claim 10 wherein the OCR feedback signal is monitored to ensure that an interface between healthy and unhealthy tissue is not near a distal tip of said guide wire assembly.

15. An RF ablation apparatus according to claim 10 wherein the OCR feedback signal is monitored to ensure that an artery wall is not near a distal tip of said guide wire assembly.

16. An RF ablation apparatus according to claim 10 wherein during a percutaneous transmyocardial revascularization procedure, the OCR feedback signal is used to monitor for an epicardium interface while myocardial tissue is being ablated.

17. A method for controlling an ablation process, using a radio frequency (RF) ablation system, the system including a radio frequency power section, an optical coherence reflectometer, a guide wire assembly optically connected to the reflectometer and electrically connected to the RF power source, the electrical connection being controlled through a control switch, said method comprising:

threading a distal tip of the guide wire assembly through diseased artery segments to lesions by percutaneous induction through a body extremity, the guide wire assembly including a guide wire, an optical fiber located within a bore of the guide wire, and an insulating coating around an outside diameter of the guide wire, the insulating coating configured such that a distal end of the guide wire and a distal end of the optical fiber are exposed;

using OCR imaging to assure an operator that the distal tip is against a lesion;

ablating the lesion by applying RF power at the distal end of the guide wire; and removing RF power upon an OCR detection of healthy tissue near the distal end of the guide wire.

18. A method according to claim 17 wherein ablating the lesion by applying RF power comprises modulating the RF power thereby allowing heat to dissipate.

19. A method for performing a transmyocardial revascularization procedure using a radio frequency (RF) ablation system, the system including a radio frequency power section, an optical coherence reflectometer (OCR), a guide wire assembly optically connected to the reflectometer and electrically connected to the RF power source, the guide wire assembly including a guide wire, an optical fiber located within a bore of the guide wire, and an insulating coating around an outside diameter of the guide wire, the insulating coating configured such that a distal end of the guide wire and a distal end of the optical fiber are exposed, the electrical connection being controlled through a control switch, said method comprising:

threading a distal tip of the guide wire assembly to an inner wall surface of a left ventricle of a heart;

applying RF power to the distal end of the guide wire;

ablating a hole within the inner wall surface; and using a signal from the OCR to stop ablation when an interface between a myocardium and epicardium is approached.

20. A method according to claim 19 wherein using a signal from the OCR to stop ablation comprises using the signal from the OCR to control the control switch thereby opening the electrical connection to the RF power source.

* * * * *